US008526600B2

(12) United States Patent
Howes et al.

(10) Patent No.: US 8,526,600 B2
(45) **Date of Patent: *Sep. 3, 2013**

(54) ANTIHELIX-CONFORMING EAR-MOUNT FOR PERSONAL AUDIO-SET

(75) Inventors: Michael Howes, Vancouver, WA (US); Dominic Amae, Vancouver, WA (US); Raymond Weikel, Camas, WA (US); Robert Jacobson, Camas, WA (US); Omer Kotzer, Portland, OR (US)

(73) Assignee: Logitech Europe S.A., Lausanne (CH)

(*) Notice: Subject to any disclaimer, the term of this patent is extended or adjusted under 35 U.S.C. 154(b) by 0 days.

This patent is subject to a terminal disclaimer.

(21) Appl. No.: 13/361,817

(22) Filed: Jan. 30, 2012

(65) Prior Publication Data

US 2012/0189154 A1 Jul. 26, 2012

Related U.S. Application Data

(63) Continuation of application No. 12/360,845, filed on Jan. 27, 2009, now Pat. No. 8,130,942, which is a continuation of application No. 10/358,120, filed on Feb. 3, 2003, now Pat. No. 7,536,008, which is a continuation-in-part of application No. 29/161,926, filed on Jun. 5, 2002, now Pat. No. Des. 470,123, and a continuation-in-part of application No. 29/161,923, filed on Jun. 5, 2002, now Pat. No. Des. 470,128, and a continuation-in-part of application No. 29/161,924, filed on Jun. 5, 2002, now Pat. No. Des. 470,122, and a continuation-in-part of application No. 29/161,922, filed on Jun. 5, 2002, now Pat. No. Des. 469,755.

(60) Provisional application No. 60/361,490, filed on Mar. 2, 2002.

(51) Int. Cl.

| | |
|---|---|
| ***H04M 9/00*** | (2006.01) |
| ***H04R 25/00*** | (2006.01) |
| ***A61B 7/02*** | (2006.01) |

(52) U.S. Cl.
USPC ....... 379/433.01; 379/430; 381/380; 181/135

(58) Field of Classification Search
USPC ......... 381/370, 374, 375, 377–380; 181/128, 181/129, 130, 135; 379/430
See application file for complete search history.

(56) References Cited

U.S. PATENT DOCUMENTS

| | | | |
|---|---|---|---|
| 3,041,856 | A | 7/1962 | Neal |
| 4,020,297 | A | 4/1977 | Brodie |

(Continued)

FOREIGN PATENT DOCUMENTS

| | | | |
|---|---|---|---|
| GB | 2277422 | A | 10/1994 |
| WO | WO 99/39544 | A1 | 8/1999 |

OTHER PUBLICATIONS

European Search/Examination Report from European Application No. 03743751.4 dated Aug. 13, 2009, 3 pages.

(Continued)

*Primary Examiner* — Tuan D Nguyen
(74) *Attorney, Agent, or Firm* — Kilpatrick Townsend & Stockton LLP

(57) ABSTRACT

A light weight and comfortable ear mount for a personal audio-set is disclosed. The ear mount conforms with the antihelix of a wearer's ear, thereby operating substantially as a compression spring between the wearer's antihelix and tragus, to operably secure the personal audio-set in place. In a preferred embodiment, the ear-mount is substantially kidney-shaped and includes an opening to prevent the total occlusion of the ear canal by the personal audio-set. Alternatively, the ear-mount includes a loop of material sized to operably engage the antihelix of the wearer's ear. The ear-mount is preferably reversible to allow it to be placed in either the wearer's left or right ear.

20 Claims, 5 Drawing Sheets

(56) References Cited

U.S. PATENT DOCUMENTS

| | | | |
|---|---|---|---|
| 5,048,090 | A | 9/1991 | Geers |
| 5,142,587 | A | 8/1992 | Kobayashi |
| 5,319,163 | A | 6/1994 | Scott |
| 5,712,453 | A | 1/1998 | Bungardt et al. |
| 6,035,961 | A | 3/2000 | Sun |
| 6,122,388 | A | 9/2000 | Feldman |
| 6,688,421 | B2 | 2/2004 | Dyer et al. |
| 7,536,008 | B2 | 5/2009 | Howes et al. |
| 2002/0096391 | A1 | 7/2002 | Smith et al. |
| 2004/0052389 | A1 | 3/2004 | Berg |
| 2004/0096075 | A1 | 5/2004 | Kuhlmann et al. |

OTHER PUBLICATIONS

International Search Report dated Jun. 17, 2003, issued in related International Application No. PCT/US03/007290.

ANTIHELIX-CONFORMING EAR-MOUNT FOR PERSONAL AUDIO-SET

CROSS-REFERENCES TO RELATED APPLICATIONS

This application is a continuation of, and claims priority to, U.S. application Ser. No. 12/360,845 entitled "Antihelix-Conforming Ear-Mount for Personal Audio-Set", filed Jan. 27, 2009, which is a continuation of U.S. application Ser. No. 10/358,120 entitled "Antihelix-Conforming Ear-Mount For Personal Audio-Set", filed on Feb. 3, 2003, which claims priority to U.S. Provisional Application No. 60/361,490 entitled "Antihelix-Conforming Ear-Mount For Personal Audio-Set", filed on Mar. 2, 2002, and which is a continuation-in-part of, and claims priority to, the following U.S. Design Applications: U.S. Design Application No. 29/161,922, filed on Jun. 5, 2002, which issued as U.S. Design Pat. No. D469,755 on Feb. 4, 2003; U.S. Design Application No. 29/161,923, filed on Jun. 5, 2002, which issued as U.S. Design Pat. No. D470,128 on Feb. 11, 2003; U.S. Design Application No. 29/161,924, filed on Jun. 5, 2002, which issued as U.S. Design Pat. No. D470,122 on Feb. 11, 2003; and U.S. Design Application No. 29/161,926, filed on Jun. 5, 2002, which issued as U.S. Design Pat. No. D470,123 on Feb. 11, 2003, all of which are incorporated herein by reference.

FIELD OF THE INVENTION

The present invention relates to a mount for a headset and the like that compresses to conform with the inner ridge of a wearer's ear known as the antihelix, thereby comfortably and detachably securing the headset in place.

BACKGROUND OF THE INVENTION

Personal audio-sets, commonly known as headphones, earphones, headsets, and the like, are gaining in popularity. The typical audio-set includes a frame containing an earphone which is usually positioned over or in a wearer's ear. In cases where the audio-set is a headset, a microphone is also typically positioned on the frame near the wearer's mouth.

It is important that the frame of the audio-set securely hold these components in their proper places with respect to the wearer, without being unduly heavy and without causing discomfort to the wearer. Historically, the frames of personal audio-sets have included a headband that the wearer positions over or behind their head to hold an earphone portion over one or both ears. However, some headband-type personal audio-sets inadvertently compress the wearer's head and/or ears thereby causing discomfort, particularly when the personal audio-set is worn for extended periods.

More recently, personal audio-sets have been mounted to a wearer without using a headband. For example, headphones have been clipped around a wearer's ear as shown in Marshall (U.S. Pat. No. 5,625,171). However, these types of mounts are relatively bulky structures and some wearers feel discomfort supporting the personal audio-set in this matter. In addition, most ear clip designs do not easily lend themselves to being worn over either a wearer's left or right ear.

Also, some personal audio-set rely on ear plug-type mounts, which are also commonly known as ear bud-type mounts, that are either physically wedged either into the wearer's ear canal or hooked on the intertragal notch of the wearer's ear as shown in Nagayoshi et al. (U.S. Pat. No. 5,544,253). However, the size of a wearer's ear and ear canal differ greatly between wearers. Accordingly, different sized ear plugs must typically be offered to account for these differences in ear and ear canal sizes. Moreover, since the entire weight of the assembly is supported by such a small portion of the ear, these types of mounts feel uncomfortable for some wearers.

In addition, in order to optimize the sound qualities of the audio-set, it is desirable for the sound pressure producing device, such as the headphone driver or other audio transducer, to be pneumatically coupled to the tympanic membrane (also known as the "eardrum") via the external auditory meatus (also known as the "ear canal"). However, many typical ear bud-type mounts permit an excessive amount of pneumatic leakage between the ear bud and the wearer's ear. This excessive leakage is usually perceived as a loss in the low frequency region of the sound transmission spectrum.

More recently, some manufacturers of ear bud-type mounts have attempted to reduce this pneumatic leakage by completely occluding the ear canal with the ear bud. While such occlusion blocks a large portion of background noise, they also tend to increase the passive attenuation of the system. Accordingly, such designs are often perceived as unnatural by the wearer. In addition, under some circumstances, such as when using a headset in an office or while driving, it is undesirable to completely block all ambient noise by occluding the ear canal with the ear bud. Accordingly, such ear bud designs tend to be undesirable for many uses.

SUMMARY OF THE INVENTION

Accordingly, despite the available improvements offered by personal audio-set ear-mounts, there remains a need for an ear-mount that is lightweight, not bulky, and comfortable to wear, that also minimizes pneumatic leakage between the ear bud and the ear without substantially increasing the passive attenuation of the system. In addition to other benefits that will become apparent in the following disclosure, the present invention fulfills these needs.

The present invention is a personal audio-set, such as a headphone, earphone, or headset, that includes a mounting portion and an ear bud. The mounting portion preferably has an ear bud mounting portion and an antihelix mounting portion. The antihelix mounting portion is preferably a band or loop of resilient material that has an opening therethrough. The band compresses into the opening to conform with the antihelix of the wearer, thereby detachably securing the personal audio-set within a wearer's ear. More preferably, the mounting portion is substantially kidney-shaped and biased to a neutral position such that the antihelix mounting portion acts like a compression spring.

The ear bud contains a headphone driver or other audio transducer (collectively referred to herein as a "speaker" or "headphone") and is operably secured to the wearer's ear at the ear's tragus. Accordingly, the weight of the audio-set is evenly distributed between a surface area of the ear defined by a relatively large portion of the wearer's antihelix at the mounting portion and the ear's tragus at the ear bud. The biasing force of the mounting portion urges the mounting portion to conform with the unique shape of each wearer's antihelix, thereby detachably securing the personal audio-set to the wearer's ear and forcing the ear bud against the wearer's tragus.

The opening in the mounting loop prevents the total occlusion of the ear canal, thereby allowing desirable ambient sounds to be heard by the wearer, while still allowing the headphone driver to remain in substantially pneumatic communication with the wearer's eardrum.

Preferably, the mounting portion and personal audio-set are shaped to fit in both a wearer's left or right ear.

DETAILED DESCRIPTION

A personal audio-set 10, such as a head phone, earphone 10' (FIGS. 8 and 13-15), or headset 10" (FIGS. 1-7, and 9-12), that includes a compressible mounting portion 12 that compresses to conform with the antihelix 90 of the wearer's ear 92 thereby detachably securing the personal audio-set 10 within the wearer's ear 92 is disclosed in FIGS. 1-15.

A. Kidney-Shaped Ear Loop

Figure 1:
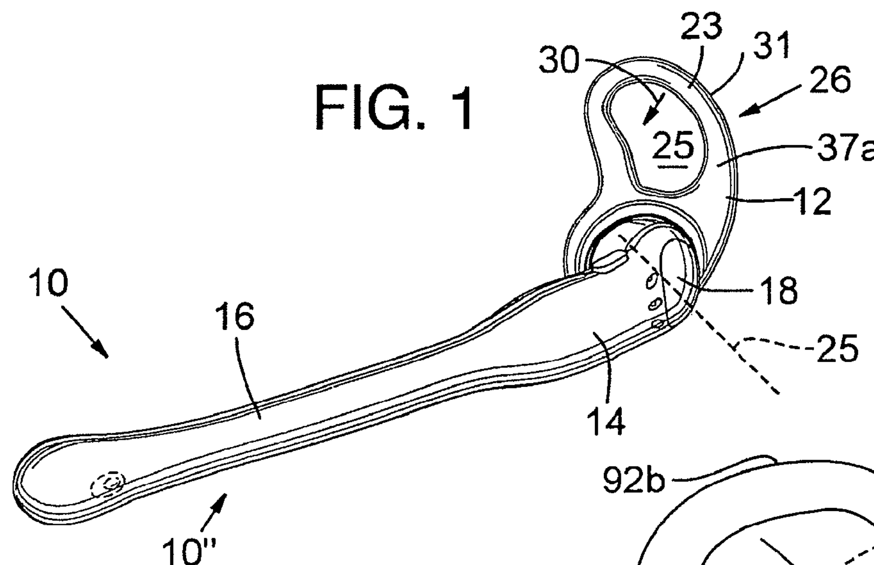
FIG. 1 is an isometric, front view of a personal audio-set having a large sized mounting portion in a neutral position and an elongate boom microphone operably secured thereto in accordance with an embodiment of the present invention.
Figure 2:
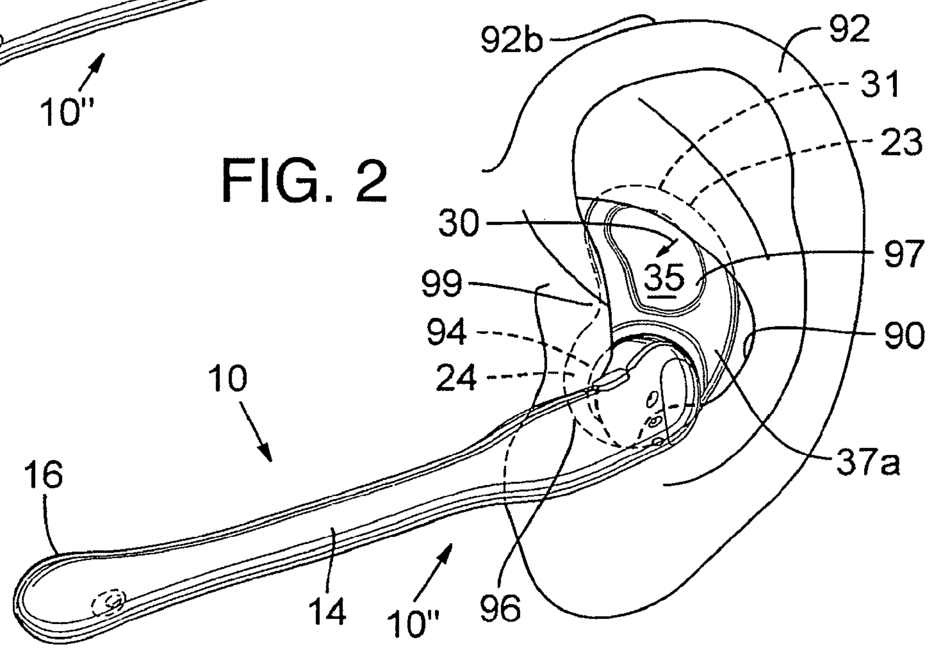
FIG. 2 is a side view of the personal audio-set of FIG. 1 showing a possible orientation with respect to a wearer's left ear.
Figure 3:
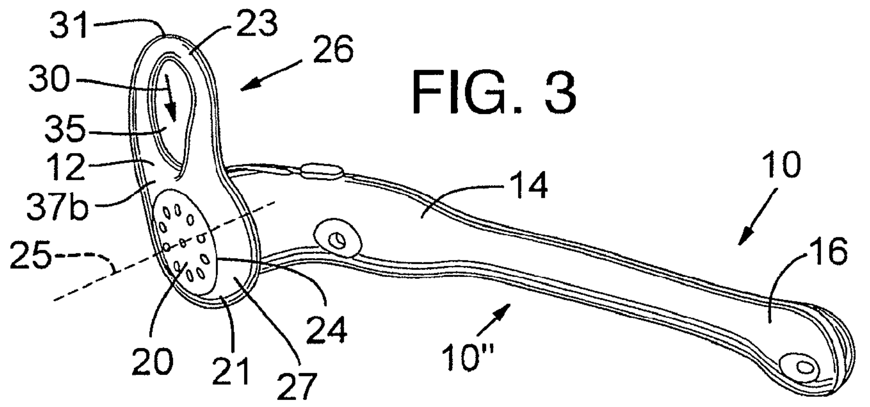
FIG. 3 is an isometric, back view of the personal audio-set of FIG. 1.
Figure 4:
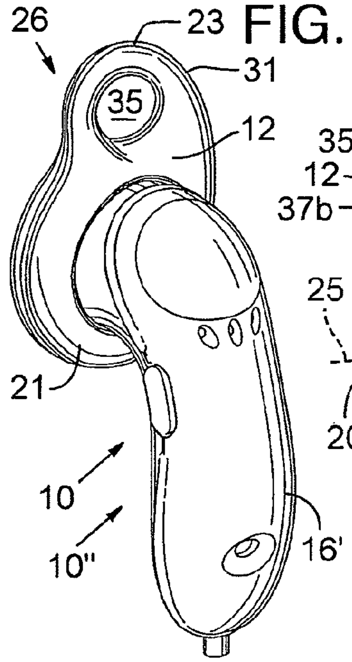
FIG. 4 is an isometric, front view of a personal audio-set having a small sized mounting portion a neutral position with a microphone operably secured thereto in accordance with an embodiment of the present invention.
Figure 5:
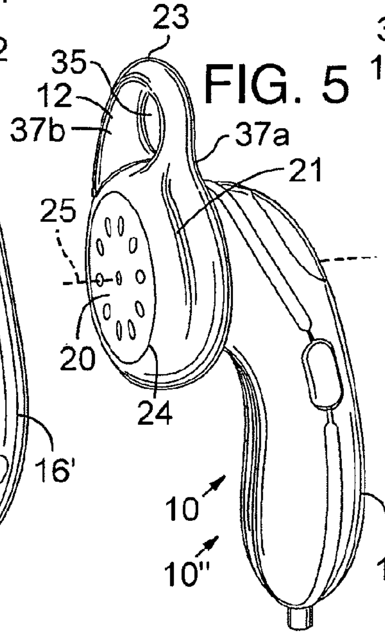
FIG. 5 is an isometric, side view of the personal audio-set of FIG. 4.
Figure 6:
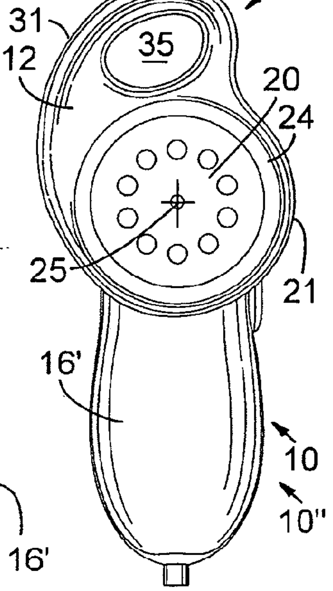
FIG. 6 is a back view of the personal audio-set of FIG. 4.

In a first preferred embodiment, shown in FIGS. 1-3, the personal audio-set 10 is a headset 10" having a frame 14 with a boom microphone 16 extending longitudinally from an ear bud 18. The ear bud 18 preferably contains driver or other audio transducer (collectively referred to herein as a "speaker 20" or earphone), and wiring (not shown) usually extends from the headset 10" to operably connect the headset 10" to an appropriate audio device (not shown).

As best shown in FIG. 2, the ear bud 18 is sized to be received within a wearer's ear 92 such that the speaker 20 is positioned over the ear canal 94 of the wearer's ear 92 with the outer portion 24 of the ear bud 18 positioned adjacent to the tragus 96 of the wearer's ear 92.

A compressible mounting portion 12, which is biased to a neutral position shown in FIG. 1, extends from the frame 14 and is operably secured to the ear bud 18. Preferably, the mounting portion 12 includes an ear bud mounting portion 21 and an antihelix mounting portion 23. The ear bud mounting portion 21 is operably secured to the ear bud 18. Preferably, the ear bud mounting portion 21 is pivotally secured around the ear bud 18 defining a pivot 25. Accordingly, the position of the frame 14 relative to the mounting portion 12 may be adjusted about the pivot 25.

More preferably, the ear bud mounting portion 21 is constructed from a resilient cushioning material such that the outer portion 27 of the ear bud mounting portion 21 contacts and cushions the wearer's ear 92. Moreover, the ear bud mounting portion 21 preferably encircles the speaker 20 and has a thickness sufficiently large to operably engage the wearer's concha 97 around the ear canal as shown, thereby providing a quasi-pneumatic seal between the speaker 20 and the wearer's ear canal.

One known material having these properties is silicone rubber. One brand of silicone rubber having particularly desirable characteristics for this purposes has a Shore A hardness of about 50, a tensile strength of about 10.5 MPa, and a Specific Gravity of about 1.13 g/cm$^3$. Such a product is commercially available. For example, the Dow Corning Corporation of Midland, Mich., USA sells such a product under the trademark SILASTIC NEW GP 500.

The antihelix mounting portion 23 extends from the ear bud mounting portion 21 and is sized to operably engage the wearer's antihelix 90. The mounting portion 12 is preferably a loop of resilient material 26 that compresses substantially in the direction of arrow 30 (FIGS. 1 and 2) to conform with the particular shape of the antihelix 90 of the wearer's ear 92. Accordingly, the mounting portion 12 functions essentially as a compression spring.

More preferably, the mounting portion 12 is substantially kidney-shaped, as best shown in FIG. 1, defining an outer edge 31 that operably engages the antihelix 90 of the wearer and a concave inner edge 33 sized to avoid the wearer's crus of helix 99. The loop of resilient material 26 preferably defines a substantially kidney-shaped opening 35 thereby allowing the loop of resilient material 26 to compress into the opening 35 during use. Moreover, this opening 35 also prevents the speaker 20 from totally occluding the ear canal thereby allowing some ambient noise to be heard by the wearer without unduly compromising the quasi-pneumatic seal between the speaker 20 and wearer's ear canal formed by the mounting portion 12. Acoustic testing has confirmed the benefits of this structure.

A wearer detachably secures the personal audio-set 10 within one of their ears 92 by compressing the mounting portion 12 substantially in the direction of arrow 30 (FIG. 1) while aligning the mounting portion 12 with their ear's antihelix 90. He or she then positions the ear bud 18 adjacent to their tragus 96 and releases the mounting portion 12. The mounting portion 12 seeks to return to its neutral position thereby urging the mounting portion 12 to conform to the shape of the antihelix 90 and urging the ear bud 18 against the wearer's tragus 96. Accordingly, the personal audio-set is secured to the wearer's ear 92, thereby securing the personal audio-set within the ear and evenly distributing the pressure along a large portion the wearer's antihelix 90 and tragus 96.

Figure 7:
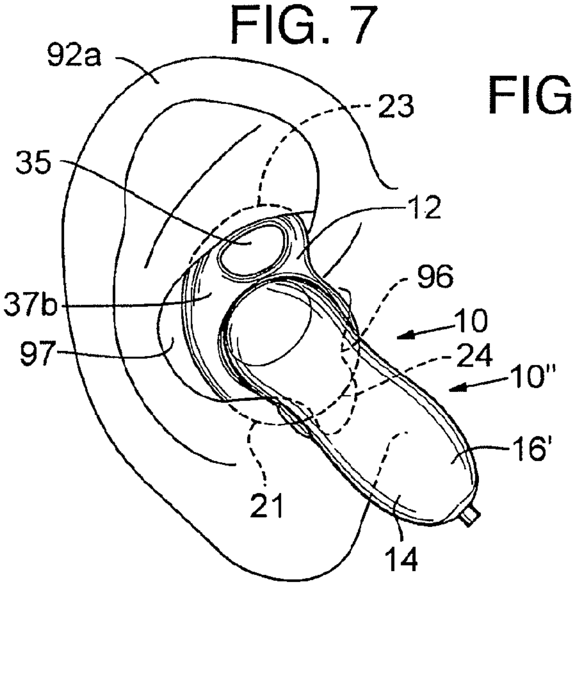
FIG. 7 is a side view of the personal audio-set of FIG. 4 showing a possible orientation with respect to a wearer's right ear.

Preferably, the mounting portion 12 is reversible so that it may fit equally well in either the wearer's left ear (92*b*, FIG. 2) or right ear (92*a*, FIG. 7). The mounting portion 12 of the present embodiment may be reversed simply by detaching the ear bud mounting portion 21 from around the ear bud 18 and turning the mounting portion 12 around so that the former exterior surface 37*a* is now the interior surface 37*b*, then re-attaching the ear bud 18 to the ear bud mounting portion 21.

Figure 8:
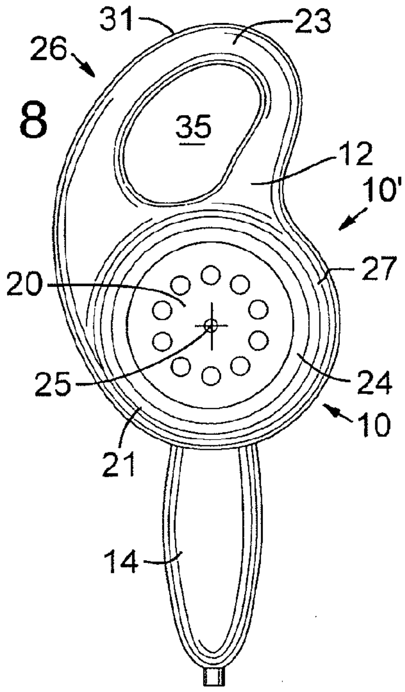
FIG. 8 is a back view of a personal audio-set with medium sized mounting portion in a neutral position and a headphone operably secured thereto in accordance with an embodiment of the present invention.

More preferably, the mounting portion is available with different sized antihelix mounting portions. For example, a mounting portion 12 having a small sized antihelix mounting portion 23 is shown in FIGS. 4-7, a medium-sized antihelix mounting portion 23 is shown in FIG. 8, and a large sized antihelix mounting portion 23 is shown in FIGS. 1-3. These different sized mounting portions are preferably sold as a set and allow a wearer the opportunity to select the optimally sized mounting portion that best conforms with their ear.

Similarly, the personal audio device operably secured to the mounting portion can be an elongate boom microphone 16 as shown in FIGS. 1-3, a shorter microphone assembly 16' as shown in FIGS. 4-7, or a simple driver 20 as shown in FIG. 8.

B. Alternative Ear Loop

Figure 9:
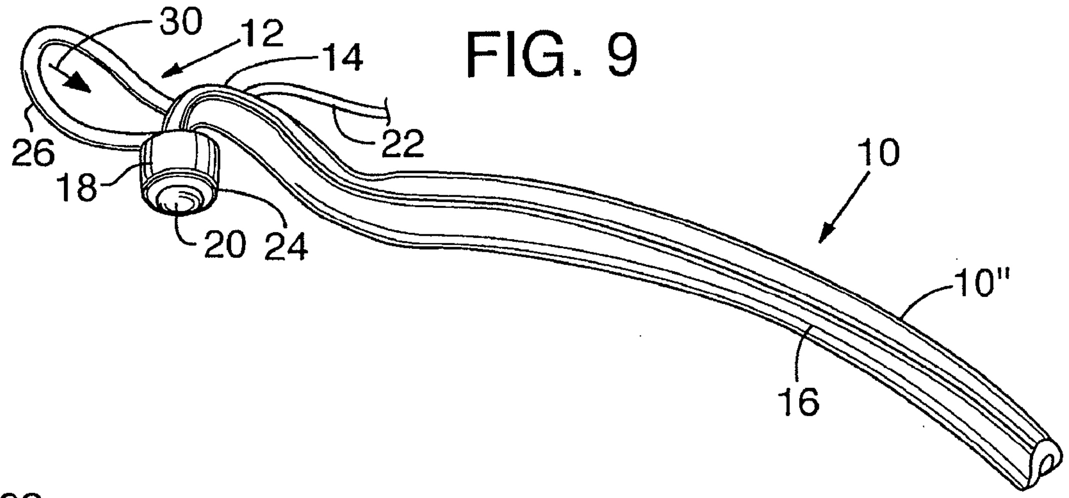
FIG. 9 is an isometric view of an alternative personal audio-set having a mounting portion in a neutral position in accordance with an embodiment of the present invention.
Figure 10:
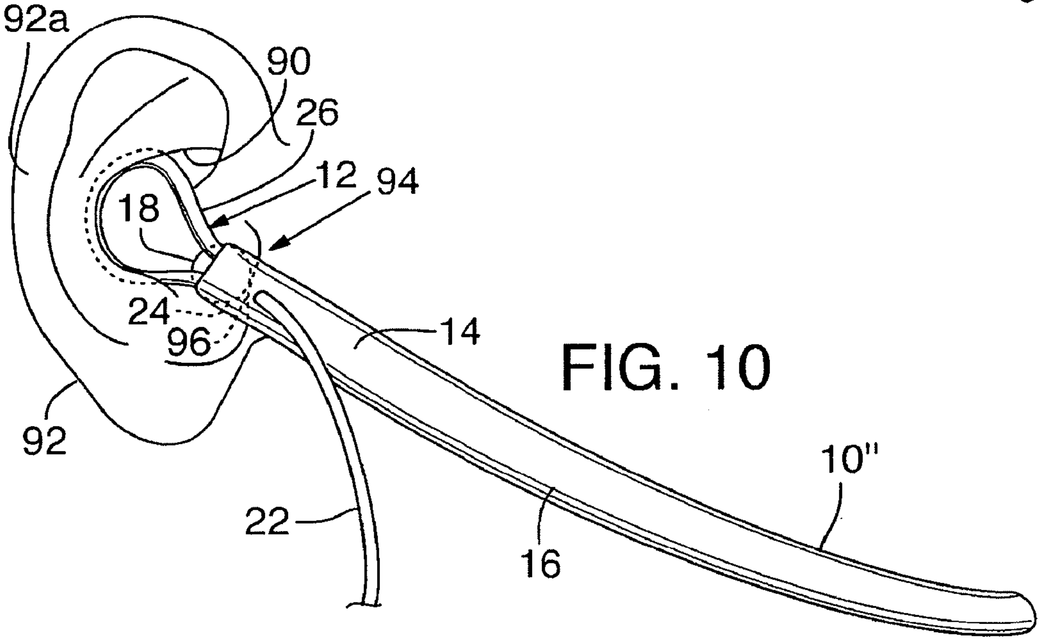
FIG. 10 is a side view of the personal audio-set of FIG. 9 showing a possible orientation with respect to a wearer's right ear.
Figure 11:
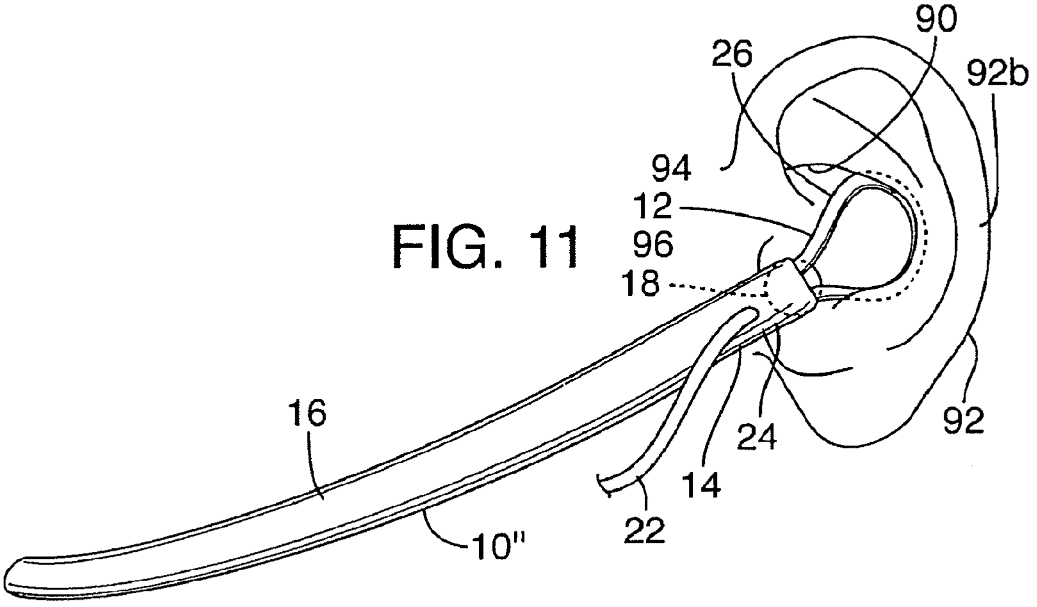
FIG. 11 is a side view of the personal audio-set of FIG. 9 showing a possible orientation with respect to a wearer's left ear.

In a first preferred embodiment, shown in FIGS. 9-11, the personal audio-set 10 is a headset 10" having a frame 14 with a boom microphone 16 extending longitudinally from an ear bud 18. The ear bud 18 preferably contains a speaker 20 and wiring 22 (FIG. 2) extends from the headset 10" to operably connect the headset 10" to an appropriate audio device (not shown).

The ear bud 18 is sized to be received within a wearer's ear 92 such that the speaker 20 is positioned over the ear canal 94 of the wearer's ear 92 with the outer portion 24 of the ear bud 18 positioned adjacent to the tragus 96 of the wearer's ear 92, as shown best shown in FIG. 2.

A compressible mounting portion 12, which is biased to a neutral position shown in FIG. 1, extends from the frame 14. Preferably, the mounting portion 12 is sized to be operably received against the antihelix 90 of the wearer's ear 92. More preferably, the mounting portion 12 is a loop of resilient material 26 that compresses in the direction of arrow 30 (FIG. 9) to conform with the particular shape of antihelix 90 of the wearer's ear 92 so as to function essentially as a compression spring.

A wearer detachably secures the personal audio-set 10 within one of their ears 92 by compressing the mounting portion 12 in the direction of arrow 30 (FIG. 9) while aligning the mounting portion 12 with their ear's antihelix 90. He or she then positions the ear bud 18 adjacent to their tragus 96 and releases the mounting portion 12. The mounting portion 12 seeks to return to its neutral position thereby urging the mounting portion 12 to conform to the shape of the antihelix 90 and urging the ear bud 18 against the wearer's tragus 96. Accordingly, the personal audio-set is secured to the wearer's ear 92.

Preferably, the ear bud 18 includes padding to comfort the connection between the ear bud 18 and the wearer's tragus 96. Similarly, the mounting portion 12 is shaped to conform with the wearer's antihelix 90, thereby evenly distributing pressure along a large portion the wearer's antihelix 90.

More preferably, the mounting portion and personal audio-set are shaped to fit in either a wearer's right ear 92*a* as shown FIG. 10 or his left ear 92*b* as shown in FIG. 11.

Figure 12:
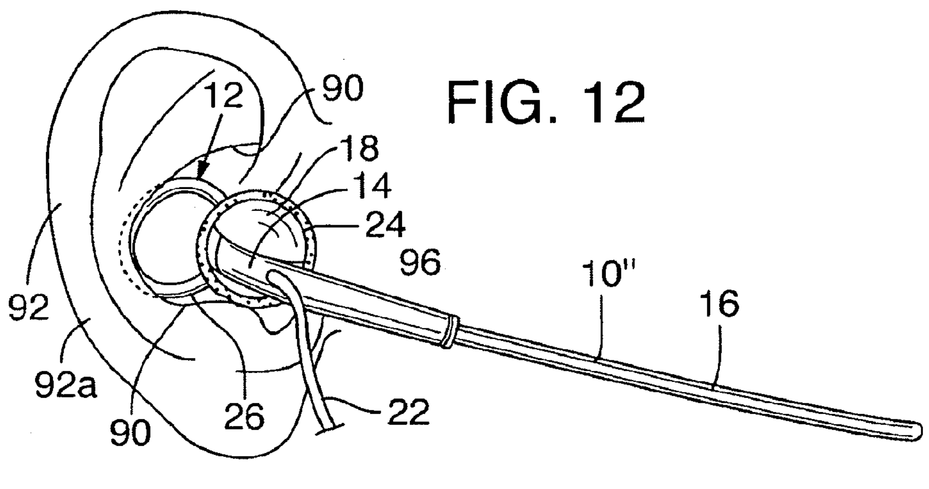
FIG. 12 is as side view of an alternative personal audio-set having an alternative ear bud and showing a possible orientation with respect to a wearer's right ear.

Referring now to FIG. 12, the ear bud 18 can also be a pad that rests over the wearer's ear canal. The pad includes an outer portion 24, sized to operably engage the tragus 96 of the wearer's ear 92 when the mounting portion is operably secured to the wearer's antihelix 90 as shown in FIG. 12.

Figure 13:
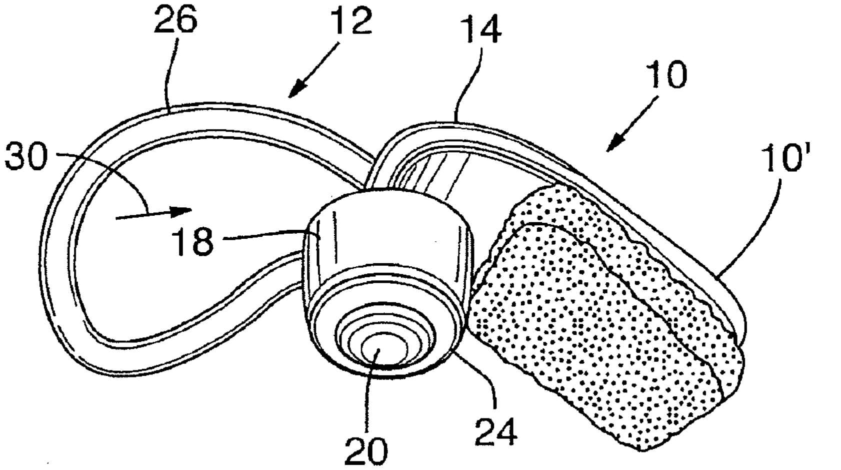
FIG. 13 is an enlarged isometric view of an alternative personal audio-set having an earphone with a mounting portion in a neutral position in accordance with an embodiment of the present invention.
Figure 14:
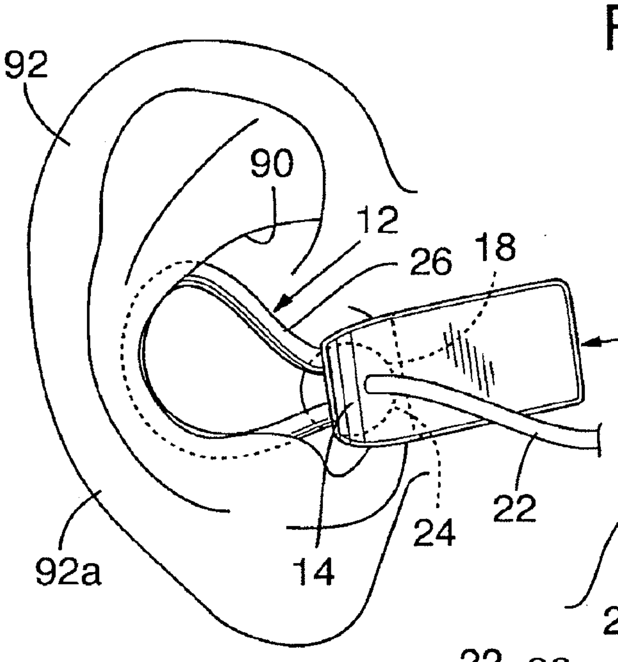
FIG. 14 is a side view of the personal audio-set of FIG. 13 showing a possible orientation with respect to a wearer's right ear.
Figure 15:
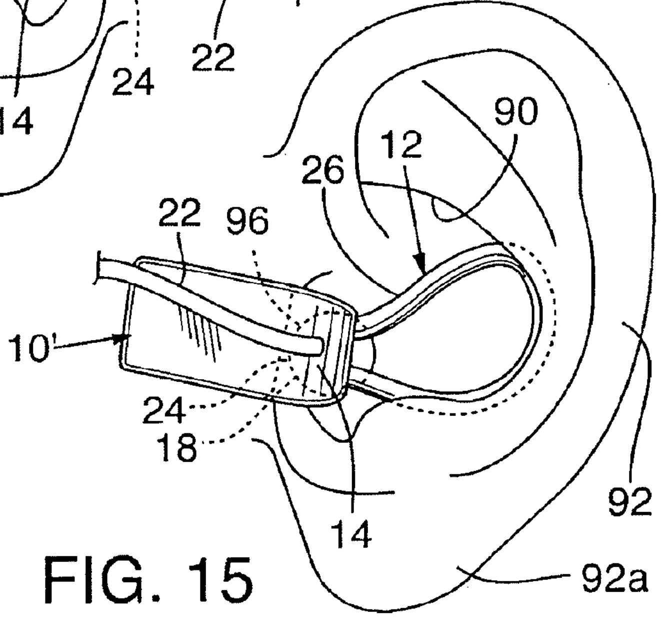
FIG. 15 is a side view of the personal audio-set of FIG. 13 showing a possible orientation with respect to a wearer's left ear.

Referring now to FIGS. 13-15, the personal audio-set 10 can also be an earphone 10' without a boom microphone extending therefrom. The earphone 10' includes a frame 14 having an ear bud 18. The ear bud preferably contains a speaker 20 and wiring 22 (FIGS. 14 and 15) extending from the earphone 10' to operably connect the earphone 10' to an appropriate audio device (not shown).

The ear bud 18 is sized to be received within a wearer's ear 92 such that the speaker 20 is positioned over the ear canal 94 of the wearer's ear 92 with the outer portion 24 of the ear bud 18 positioned adjacent to the tragus 96 of the wearer's ear 92, as best shown in FIG. 14 (right ear 92*a*) and FIG. 15 (left ear 92*b*). The mounting portion 12 of the first preferred embodiment is operably secured to the frame 14, thereby allowing the earphone 10' to be detachably secured to either the wearer's right or left ears 92*a* or 92*b*, respectively.

If desired, separate earphones 10' can be secured in both the right and left ears 92*a* and 92*b*, respectively, of the wearer, thereby providing stereo sound to the wearer, and allowing the two earphones 10' to operate like a pair of headphones.

Having described and illustrated the principles of our invention with reference to a preferred embodiment thereof, it will be apparent that the invention can be modified in arrangement and detail without departing from such principles. In view of the many possible embodiments to which the principles may be put, it should be recognized that the detailed embodiment is illustrative only and should not be taken as limiting the scope of our invention. Accordingly, we claim as our invention all such modifications as may come within the scope and spirit of the following claims and equivalents thereto.

What is claimed is:

1. A personal audio set for detachably securing to the ear of a wearer, the ear having an antihelix, ear canal, and tragus, said personal audio set comprising:

a frame containing an audio transducer and an ear bud extending therefrom;

a substantially compressible mounting portion biased to a neutral position, detachably secured to the frame, and sized to operably engage the antihelix of the wearer's ear, said mounting portion having an elongated portion, said elongated portion being substantially compressible and defining a first, non-pivoting, direction from said frame;

wherein said elongated portion of said mounting portion conforms to the shape of the antihelix of the wearer's ear and urges the ear bud toward the tragus of the wearer's ear thereby aligning the audio transducer over the wearer's ear canal and operably securing the personal audio set to the wearer's ear.

2. The personal audio set for detachably securing to the ear of a wearer of claim 1, wherein said personal audio set is reversible so that it may be operably secured to one of said left and right ears of the wearer.

3. The personal audio set for detachably securing to the ear of the wearer of claim 1, wherein said personal audio set is a headset.

4. The personal audio set for detachably securing to the ear of the wearer of claim 1, wherein said personal audio set includes an elongate boom microphone extending from the frame.

5. The personal audio set for detachably securing to the ear of the wearer of claim 1, wherein said personal audio set is a headphone.

6. An ear mount for a personal audio set having an ear bud with an audio transducer therein, said ear mount having:

an ear bud mounting portion for pivotally securing the ear bud to the ear mount; and a substantially compressible antihelix mounting portion sized to operably engage an antihelix of a wearer's ear and extending from said ear bud mounting portion, said antihelix mounting portion biased to a neutral position and having an elongated portion, said elongated portion substantially compressible from said neutral position in a non-pivoting direction relative to said ear bud such that said elongated portion of said antihelix mounting portion urges the ear bud away from said antihelix toward the tragus of the wearer's ear such that the ear bud is aligned over the ear canal, thereby securing the audio set to the wearer's ear; and wherein said ear bud mounting portion operably engages the concha of the wearer's ear, thereby providing a quasi-pneumatic seal between the audio transducer and the ear canal of the wearer.

7. The ear mount of claim 6, wherein said ear mount is a monolithic structure.

8. The ear mount of claim 6, wherein said ear mount is constructed of silicone rubber.

9. The ear mount of claim 6, wherein said ear mount has a curved outer edge for operably engaging the antihelix of the wearer's ear, and a concave inner edge size to avoid the crus of helix of the wearer's ear.

10. The ear mount of claim 6, wherein said antihelix mounting portion is a compression spring.

11. The ear mount of claim 6, further including a loop of material defining the antihelix mounting portion, said loop of material defining an opening.

12. The ear mount of claim 11, wherein said antihelix mounting portion is a loop of material extending from said ear bud mounting portion.

13. The ear mount of claim 11, wherein said ear bud mounting portion encircles the ear bud.

14. The ear mount of claim 6, wherein said ear mount is reversible so that it may be detachably secured to one of a left ear and a right ear of the wearer.

15. The ear mount of claim 6, wherein said antihelix mounting portion is a loop of material extending from said ear bud mounting portion.

16. A plurality of ear mounts for a personal audio set having an ear bud with an audio transducer therein, each ear mount of said plurality of each mounts having:

an ear bud mounting portion for operably securing the ear bud to the ear mount; and a substantially compressible antihelix mounting portion sized to operably engage an antihelix of a wearer's ear and extending from said ear bud mounting portion, said antihelix mounting portion biased to a neutral position and having an elongated portion, said elongated portion compressible from said neutral position in a non-pivoting direction relative to said ear bud such that said elongated portion of said antihelix mounting portion urges the ear bud away from said antihelix toward the tragus of the wearer's ear, thereby securing the audio set to the wearer's ear such that the ear bud is aligned over the ear canal;

wherein each ear mount of said plurality of ear mounts is a different size and a wearer may select one of said plurality of ear mounts that best fits the wearer's ear; and wherein said ear bud mounting portion operably engages the concha of the wearer's ear, thereby providing a quasi-pneumatic seal between the audio transducer and the ear canal of the wearer.

17. The plurality of ear mounts of claim 16, wherein at least one ear mount of said plurality of ear mounts further includes a loop of material defining the antihelix mounting portion, said loop of material defining an opening.

18. The plurality of ear mounts of claim 16, wherein each ear mount is reversible so that it may be detachably secured to one of a left ear and a right ear of the wearer.

19. The plurality of ear mounts of claim 16, wherein at least one ear mount of said plurality of ear mounts is a monolithic structure.

20. The plurality of ear mounts of claim 16, wherein at least one ear mount of said plurality of ear mounts has a curved outer edge for operably engaging the antihelix of the wearer's ear, and a concave inner edge size to avoid the crus of helix of the wearer's ear.

* * * * *